United States Patent [19]

Potaczek

[11] 4,359,047
[45] Nov. 16, 1982

[54] GELATINOUS ARTICLES AND COMPOSITIONS

[75] Inventor: Jan J. Potaczek, Leicester, England

[73] Assignee: Advance Tapes (U.K.) Limited, Leicester, England

[21] Appl. No.: 131,891

[22] Filed: Mar. 20, 1980

[30] Foreign Application Priority Data

Mar. 21, 1979 [GB] United Kingdom ............... 7909957

[51] Int. Cl.$^3$ ..................... A61F 5/44; A61L 15/06
[52] U.S. Cl. ............................ 128/156; 128/283; 106/208; 106/209; 523/111; 523/121; 524/498; 524/548; 525/54.1; 525/54.3; 525/384; 525/194; 525/207; 525/327.7; 525/328.9; 536/114
[58] Field of Search ............... 106/208, 13.5, 137, 106/209; 260/17.4 ST, 8, 117; 128/156, 283; 525/329, 384, 54.3, 194, 54.1, 207; 536/114; 524/498, 548; 523/111

[56] References Cited

U.S. PATENT DOCUMENTS

| | | | |
|---|---|---|---|
| 2,997,464 | 8/1961 | Sellers | 260/78.5 |
| 3,245,933 | 4/1966 | Muskat | 260/29.6 |
| 3,640,741 | 2/1972 | Etes | 106/170 |
| 3,805,789 | 4/1974 | Marsan | 128/283 |
| 3,878,151 | 4/1975 | Dachs | 260/29.6 T |
| 3,908,658 | 9/1975 | Marsan | 128/283 |
| 3,980,084 | 9/1976 | Kross | 128/283 |
| 3,983,095 | 9/1976 | Bashaw | 526/15 |

FOREIGN PATENT DOCUMENTS 2441626 3/1975 Fed. Rep. of Germany .
2277597 6/1976 France .
2392076 12/1978 France .
2393566 5/1979 France .
2429251 1/1980 France .
1307968 2/1973 United Kingdom .

OTHER PUBLICATIONS

Chemical Abstracts, vol. 81, No. 12, p. 119, No. 65513 (9/23/74).
Whistler, "Industrial Gums", 1973, p. 248.

*Primary Examiner*—Allan Lieberman
*Assistant Examiner*—Pat Short
*Attorney, Agent, or Firm*—W. R. Hulbert

[57] ABSTRACT

A gelatinous adhesive composition and a tacky article of manufacture are produced by heating at least one polyhydric alcohol and at least one material selected from the group consisting of naturally occurring high molecular weight polysaccharide gums, other than gum Karaya, and resins which are a copolymer of a vinyl ether and a second component selected from maleic anhydride and its corresponding free acid, together in the absence of solvent to promote chemical reaction between the components and to drive off water produced in the reaction, the reaction being carried substantially to completion. In another embodiment, the components are at least one polyhydric alcohol, a resin which is a copolymer of a vinyl ether and a second component selected from maleic anhydride and its corresponding free acid, and a material selected from the group consisting of gelatin and naturally occurring high molecular weight polysaccharide gums.

26 Claims, No Drawings

GELATINOUS ARTICLES AND COMPOSITIONS

DESCRIPTION

This invention relates to gelatinous articles and compositions. More particularly it is concerned with certain novel gelatinous tacky articles of manufacture and with certain new gelatinous adhesive compositions useful, for example, in protective plasters or dressings as a tackifying agent. As will be explained below, the articles may for example be embodied as protective plasters or dressings as such, or as rings, washers or the like in surgical appliances such as ostomy appliances.

Conventional pressure-sensitive plasters comprise an adhesive based on a rubber/resin mixture. Such plasters adhere with difficulty to moist body surfaces and, even then, under movement of the body they may easily detach from the skin. There is a particular need for improved protective plasters which may be used in the management of colostomies and ileostomies and similar surgical operations. The ostomy appliances provided for patients who have had such an operation have generally included a sealing ring supposedly for preventing draining waste material which commonly includes active gastric juices from coming into contact with the patient's skin surrounding the stoma, and thereby attacking the skin, or from leaking thereby producing embarrassing odour and soiling of the patient's clothing. Such ostomy sealing rings have not always proved reliable and additional sealing compositions in paste form which may be squeezed from a toothpaste-like tube have been suggested to overcome this problem but have not found wide application, being difficult for the patient himself to use.

In co-pending patent application Ser. No. 132,071 ("Articles of Manufacture having Adhesive Properties") filed the same day as this Application and which claims priority from our earlier British Application No. 7909956, we describe novel articles of manufacture comprising a gelatinous adhesive composition dispersed in a plastics matrix. Protective plasters and dressings, and rings, washers and the like for use with surgical appliances, and produced as articles of manufacture in accordance with the teachings of our aforesaid copending application, possesses significantly improved properties as compared with those plasters, dressings, rings, washers and the like of which we are aware and which have been sold in the British market.

The present invention is primarily concerned with the adhesive compositions themselves which possess utility per se in addition to their substantial utility as intermediates in the production of articles of manufacture in accordance with our aforesaid co-pending application.

We have also found that the physical properties of the adhesive compositions may readily be adjusted, as we shall explain in detail below, to enable the production of articles of manufacture such as protective plasters and dressings (with or without a protective backing sheet), and rings, washers and the like for surgical appliances, for example ostomy appliances, without the composition requiring first to be dispersed in a plastics matrix.

We are aware of so-called "Karaya washers" which have been widely sold for use in ostomy appliances, and which are produced by mixing Karaya powder and glycerol and moulding the mixture at about 120° C. to produce a gelatinous ring. We accordingly make no claim herein to inventiveness in respect of articles of manufacture consisting of the reaction product of these two ingredients alone. Karaya gum is both relatively expensive and in short supply in that it is obtained from the bark of a tree found only in limited areas of the world. There is a substantial need for satisfactory or better alternatives to such Karaya washers which are not dependent (or are at least less dependent) on supplies of Karaya gum to meet the growing demand for gelatinous tacky rings, washers, and the like, for use with surgical appliances. So far as we are aware, until the present invention this need has remained unsatisfied.

The present invention accordingly sets out to provide, in other aspects thereof novel articles of manufacture which do satisfy this need.

In a first aspect of the present invention, we provide a gelatinous tacky article of manufacture produced by heating (a) one or more polyhydric alcohols and (b) One or more naturally occurring high molecular weight polysaccharide gums, other than gum Karaya, and/or a resin which is a copolymer of a vinyl ether and an organic acid anhydride and/or its corresponding free acid, together to promote chemical reaction between components (a) and (b).

In a second and alternative aspect of the invention, we provide a gelatinous tacky article of manufacture produced by heating (a) one or more polyhydric alcohols and (b) a resin which is a copolymer of a vinyl ether and an organic acid anhydride and/or its corresponding free acid and (c) gelatin and/or one or more naturally occurring high molecular weight polysaccharide gums, together to promote chemical reaction between component (a) and components (b) and (c).

This invention provides in a third alternative aspect thereof, a gelatinous adhesive composition produced by heating (a) one or more polyhydric alcohols and (b) one or more naturally occurring high molecular weight polysaccharide gums, other than gum Karaya, and/or a resin which is a copolymer of a vinyl ether and an organic acid anhydride and/or its corresponding free acid, together to promote chemical reaction between components (a) and (b).

In a further alternative aspect thereof, the invention provides a gelatinous adhesive composition produced by heating (a) one or more polyhydric alcohols and (b) a resin which is a copolymer of a vinyl ether and an organic acid anhydride and/or its corresponding free acid and (c) gelatin and/or one or more naturally occurring high molecular weight polysaccharide gums, together to promote chemical reaction between component (a) and components (b) and (c).

Suitable polyhydric alcohols include but are not limited to glycerol, sorbitol, polyvinylalcohol and pentaerythritol.

The preferred resin is a methyl vinyl ether/maleic anhydride copolymer of which a range of suitable resins is available under the trade name Gantrez from Gaf (G.B) Limited and under the trade name Viscofas from Imperial Chemical Industries Ltd. We prefer to use Gantrez AN139 or Viscofas L.30.

A number of naturally occurring high molecular weight polysaccharide gums which may be used in the practise of this invention are readily available. Examples of gums which we have found can be useful in the practise of this invention include gum Tragacanth and gum Arabic (gum Acacia).

The chemical reaction which occurs on heating between components (a) and (b) or between component (a) and both components (b) and (c) is essentially ester formation.

Adhesive compositions and tacky articles of manufacture produced in accordance with this invention are water-absorbing (swellable) hydrocolloids. The gelatinous adhesive compositions can be made either in a heated reaction vessel or in situ during blending with other ingredients in a heated Z-blade mixer, as for example in forming a desired article of manufacture in accordance with our aforesaid copending application, the blend being subsequently allowed to solidify, suitably in a mould. A gelatinous tacky article of manufacture in accordance with the present invention is suitably made by heating the components in a heated reaction vessel for an appropriate period of time and then allowing the mass to solidify, suitably in a mould.

The specific gel content of the gelatinous adhesive composition may readily be adjusted to obtain a desired degree of water swelling (absorbing) capability. The gel structure may be altered by varying the proportions of the reacting ingredients and by employing a crosslinking agent such as glyoxal or citric acid. Melamine resin is also an effective crosslinking agent for the composition but may sensitise the skin of some people and is therefore less preferred.

Our gelatinous adhesive compositions have very useful inherent pressure-sensitive properties, enabling them to act as the sole or main tackifying agent in adhesive articles, such as protective plasters or dressings, or rings, washers, or the like, in surgical appliances such as ostomy appliances. The resultant articles adhere readily to dry or moist body surfaces.

We have found that particularly satisfactory ostomy plasters result by blending a gelatinous adhesive composition in accordance with this invention and in an amount from 30 to 55 percent by weight of the total weight with a suitable plastics matrix as described in our aforesaid copending patent application. The ostomy plasters we have made from this blend are soft and pliable, have good adhering qualities to dry and moist skin, and are resistant to plastic flow at body temperature.

Ostomy plasters may also be made as articles of manufacture in accordance with the present invention by adjusting the physical characteristics of the composition appropriately and then pressing the composition to a thin adhesive sheet in an hydraulic press, which sheet may be cut into shapes required. Such plasters, too, have been found to have excellent properties.

When an adhesive article in accordance with this invention is embodied as a protective plaster or dressing, it preferably has a backing sheet to prevent the tacky plaster or dressing from sticking to clothing etc. A thin, suitably water impermeable, plastics film, for example of polyethylene may be employed. The film is suitably provided with perforations which assist in getting rid of occluded air bubbles during the lamination process.

The physical characteristics of our adhesive articles/compositions, such as tack, plasticity, cohesive strength and moisture absorbance, may be modified by admixing other substances such as: viscosity modifiers, e.g., micronised silica; tack modifiers, e.g., polyvinylpyrrolidone resin (which in glycerol forms a tacky viscous compound); fillers e.g., calcium carbonate; crosslinking agents, e.g., glyoxal or citric acid, anti-microbial agents; and plasticisers, e.g., paraffin oil. Selection of the polyhydric alcohol may also be used to adjust the physical properties of the articles/compositions. Thus while the presence of glycerol alone may eventually result in the composition dissolving, substitution wholly or partially by sorbitol may avoid this. Pentaerythritol is not soluble to any great extent. The presence of polyvinylalcohol enhances adhesion to the skin.

Several examples which illustrate the invention now follow. Of these, Examples 1 to 5 describe the production of our adhesive composition in situ while blending with other ingredients.

EXAMPLE 1

300 Grams of high molecular weight ethylene/vinyl acetate copolymer, manufactured by Bayer AG under the trade name Levapren L452, and 100 grams of low molecular weight ethylene/vinyl acetate copolymer, manufactured by Bayer AG under the trade name Levapren KH 8160, were placed in a Z-blade mixer heated at 80°–90° C. and mixed until a uniform dough was obtained. Then 85 grams of glycerine, 20 grams of Gantrez AN 139 (methyl vinyl ether/maleic anhydride copolymer resin sold by Gaf (GB) Limited, 60 grams of Karaya gum and 2 grams of Nipastat (a mixture of p-hydrobenzoic acid esters produced by Nipa Laboratories Limited and having anti-microbial properties) were added and mixed for one hour at 80°–90° C., when at the end of this period a uniform dispersion of the gelatinous adhesive composition were obtained in the plastics matrix. Part of the dispersion was pressed to a thin sheet in an hydraulic press maintained at 130° C. The thus formed adhesive sheet was laminated to a perforated thin polyethylene film and then cut into plasters of desired shapes and sizes. The remainder of the dispersion was moulded to produce a solid mass.

EXAMPLE 2

The procedure of Example 1 was repeated but with the quantity of Nipastat reduced to 1 gram. Comparison of the products of the two examples show that the reduced Nipastat composition was less likely to sensitise skin.

EXAMPLE 3

300 Grams of Levapren L452 and 300 grams of Levapren KH 8160 were placed in a Z-blade mixer heated at 80°–90° C. and mixed until a uniform dough was obtained. Then 450 grams of glycerine, 60 grams of Kollidon 90 (polyvinyl pyrrolidone resin manufactured by BASF Limited), 150 grams of Gantrez AN139 and 2 grams of Nipastat were added and mixed for one hour at 80°–90° C. Part of the dispersion was pressed to a thin sheet in an hydraulic press maintained at 130° C., and the resultant adhesive sheet laminated to a perforated thin polythene film. Satisfactory ostomy plasters were obtained.

EXAMPLE 4

The procedure of Example 3 was repeated but with the Nipastat content reduced to 1 gram. Comparison of the resulting ostomy plasters showed that those of Example 4 exhibited less likelihood of sensitising skin as compared with those of Example 3.

EXAMPLE 5

1500 Grams of Vistanex LM-MH (a polyisobutylene viscous resin sold by Esso Chemical Co. Ltd.) and 500 grams of Levapren 452 were placed in a Z-blade mixer heated at 90°–100° C. and mixed until a uniform plastics dough was obtained. Then 900 grams of gum Tragacanth, 600 grams of glycerol, 400 grams of sorbitol and 2 grams of Nipastat were added and mixed for one hour at 90°–100° C., when at the end of this time a uniform dispersion of the hydrocolloid in the plastics matrix was obtained. Part of the dispersion was pressed to a thin sheet in a hydraulic press maintained at 120° C. The resulting adhesive sheet was laminated to perforated thin polyethylene film and then converted into plasters of desired shapes and sizes. Satisfactory ostomy plasters were obtained.

EXAMPLE 6

40 Grams of glycerine and 35 grams of gum Tragacanth were placed in a glass jar and heated at 110° C. in an oven for 2 hours, stirring the contents every 15 minutes. At the end of the curing cycle a thick viscous mass resulted. Part of this glycerine/Tragacanth adhesive composition was blended with about the same weight of a mixture of equal parts of Levapren L452 and Levapren KH 8160 and moulded in an open dished mould at 120° C. to produce an ostomy sealing ring or washer. A second part of the composition was moulded without further addition in a similar mould to produce a semisolid tacky gelatinous ring. A third part was pressed in an hydraulic press at about 130° C. to yield a thin adhesive sheet.

EXAMPLE 7

The procedure of Example 6 was followed except that instead of 35 grams of gum Tragacanth, there was substitued a mixture of 27 grams of gum Acacia and 2 grams of Madurit 5458 (a melamine resin manufactured by Hoechst of Germany) as crosslinking agent.

EXAMPLE 8

Example 7 was repeated first with 2 grams of citric acid substituted for the Madurit 5458 and second with 2 grams of glyoxal obtained from BDH Chemicals Ltd. substituted for the Madurit 5458. The products resulting were found superior in each case to those of Example 6 in being less likely to induce sensitivity in skin.

EXAMPLE 9

200 Grams of sorbitol and 200 grams of gum Tragacanth were placed in a glass container and heated at 120° C. in an oven for one hour, stirring the contents every 15 minutes. After cooling to room temperature, a solid mass resulted. This product was shown to be a hydrocolloid, swelling in contact with water. A portion was pressed to a thin sheet in an hydraulic press.

A further 200 grams of the sorbitol/gum Tragacanth hydrocolloid was blended with 150 grams of Vistanex LM-MH and 50 grams of Levapren 452 and moulded in an open dished mould at 120° C. to produce an ostomy sealing ring.

EXAMPLE 10

The procedure of Example 9 was repeated first with 200 grams of pentaerythritol and second with 200 grams of polyvinylalcohol substituted for the sorbitol and the results compared. The ostomy sealing rings formed using pentaerythritol tended to remain relatively hard and not greatly to swell absorbing moisture when in contact with the skin and are therefore in our view less preferable. The rings formed with polyvinylalcohol exhibited particularly good adhesion to skin.

Pressure-sensitive plasters produced in accordance with this invention or by dispersing an adhesive composition in accordance with this invention in a plastics matrix are useful in the management of colostomies and ileostomies. We have found that the specific plasters described adhere firmly and for extended periods of time to moist human body surfaces. Unlike conventional pressure-sensitive plasters comprising an adhesive based on a rubber-resin mixture, our plasters will adhere firmly over long periods of time. They are soft and pliable, conform to the contours of the body surface and do not peel or detach even from moist skin during the normal activities of the person wearing them. Indeed moisture seems to assist adhesion.

Articles having inherent pressure-sensitive characteristics can readily be moulded in a variety of shapes and configurations by following our techniques. The specific examples given are not intended to be limiting.

When the rings or washers are to be used in ostomy appliances, a base such as aluminium hydroxide may be added to the composition prior to moulding to neutralize acid present in the drainage into the appliance.

What I claim is:

1. A gelatinous tacky article of manufacture produced by heating
    (a) at least one polyhydric alcohol and
    (b) at least one material selected from the group consisting of naturally occurring high molecular weight polysaccharide gums, other than gum Karaya, and resins which are a copolymer of a vinyl ether and a second component selected from maleic anhydride and
its corresponding free acid, together in the absence of solvent to promote chemical reaction between components (a) and (b) and to drive off water produced in the reaction, the reaction being carried substantially to completion.

2. An article according to claim 1, wherein the naturally occurring high molecular weight polysaccharide gums are selected from the group consisting of gum Tragacanth and gum Arabic (gum Acacia).

3. A gelatinous tacky article of manufacture produced by heating
    (a) at least one polyhydric alcohol and
    (b) a resin which is a copolymer of a vinyl ether and a second component selected from maleic anhydride and its corresponding free acid and
    (c) a material selected from the group consisting of gelatin and naturally occurring high molecular weight polysaccharide gums,
together in the absence of solvent to promote chemical reaction between component (a) and components (b) and (c) and to drive off water produced in the reaction, the reaction being carried substantially to completion.

4. An article according to claim 3, wherein the naturally occurring high molecular weight polysaccharide gums are selected from the group consisting of gum Karaya, gum Tragacanth, and gum Arabic (gum Acacia).

5. An article according to claim 1 or claim 3, wherein the at least one polyhydric alcohol is selected from glycerol, sorbitol, pentaerythritol and polyvinylalcohol.

6. An article according to claim 1 or claim 3, wherein the said copolymer resin comprises a copolymer of a methyl vinyl ether and a second component selected from maleic anhydride and its free acid.

7. An article according to claim 1 or claim 3, wherein the physical characteristics of the said article including tack, plasticity, cohesive strength and moisture absorbency are modified by the incorporation into said article of at least one material selected from viscosity modifiers, tack modifiers, fillers, crosslinking agents, antimicrobial agents, and plasticisers.

8. An article according to claim 7, wherein micronised silica is present as a viscosity modifier.

9. An article according to claim 7, wherein polyvinylpyrrolidone resin is present as a tack modifier.

10. An article according to claim 7, wherein the crosslinking agent is selected from glyoxal, citric acid, and melamine resin.

11. An article according to claim 7, wherein paraffin oil is present as a plasticiser.

12. An article according to claim 1 or claim 3, when moulded to form a component of a surgical appliance or the like.

13. An article of manufacture according to claim 1 or claim 3 moulded to form an ostomy, ring or washer.

14. A plaster or protective dressing consisting of an article of manufacture according to claim 1 or claim 3 which has been pressed to a thin adhesive sheet in an hydraulic press and then cut into required shapes.

15. A plaster or protective dressing according to claim 14 provided with a backing sheet in the form of a thin water impermeable plastics film, for example of polyethylene.

16. A gelatinous adhesive composition produced by heating
   (a) at least one polyhydric alcohol and
   (b) at least one material selected from the group consisting of naturally occurring high molecular weight polysaccharide gums, other than gum Karaya, and resins which are a copolymer of a vinyl ether and a second component selected from maleic anhydride and its corresponding free acid,
together in the absence of solvent to promote chemical reaction between components (a) and (b) and to drive off water produced in the reaction, the reaction being carried substantially to completion.

17. A gelatinous adhesive composition according to claim 16, wherein the naturally occurring high molecular weight polysaccharide gums are selected from the group consisting of gum Tragacanth and gum Arabic (gum Acacia).

18. A gelatinous adhesive composition produced by heating
   (a) at least one polyhydric alcohol and
   (b) a resin which is a copolymer of a vinyl ether and a second component selected from maleic anhydride and its corresponding free acid and
   (c) a material selected from the group consisting of gelatin and naturally occurring high molecular weight polysaccharide gums,
together in the absence of solvent to promote chemical reaction between component (a) and components (b) and (c) and to drive off water produced in the reaction, the reaction being carried substantially to completion.

19. A composition according to claim 18, wherein the naturally occurring high molecular weight polysaccharide gums are selected from the group consisting of gum Karaya, gum Tragacanth, and gum Arabic (gum Acacia).

20. A composition according to claim 16 or claim 18, wherein the polyhydric alcohol is selected from glycerol, sorbitol, pentaerythritol and polyvinylalcohol.

21. A composition according to claim 16 or claim 18, wherein the said copolymer resin comprises a copolymer of a methyl vinyl ether and a second component selected from maleic anhydride and its free acid.

22. A composition according to claim 16 or claim 18, wherein the physical characteristics of the said composition including tack, plasticity, cohesive strength and moisture absorbency are modified by the incorporation into said composition of at least one material selected from viscosity modifiers, tack modifiers, fillers, crosslinking agents, antimicrobial agents, and plasticisers.

23. A composition according to claim 22, wherein micronised silica is present as a viscosity modifier.

24. A composition according to claim 22, wherein polyvinylpyrrolidone resin is present as a tack modifier.

25. A composition according to claim 22, wherein the crosslinking agent is selected from glyoxal, citric acid, and melamine resin.

26. A composition according to claim 22, wherein paraffin oil is present as a plasticiser.

* * * * *